US011232935B2

(12) United States Patent
Ikegami et al.

(10) Patent No.: US 11,232,935 B2
(45) Date of Patent: Jan. 25, 2022

(54) MASS SPECTROMETRY DATA PROCESSING DEVICE

(71) Applicant: SHIMADZU CORPORATION, Kyoto (JP)

(72) Inventors: Masahiro Ikegami, Kyoto (JP); Koretsugu Ogata, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 535 days.

(21) Appl. No.: 16/329,925

(22) PCT Filed: Sep. 1, 2016

(86) PCT No.: PCT/JP2016/075724
§ 371 (c)(1),
(2) Date: Mar. 1, 2019

(87) PCT Pub. No.: WO2018/042605
PCT Pub. Date: Mar. 8, 2018

(65) Prior Publication Data
US 2019/0198304 A1 Jun. 27, 2019

(51) Int. Cl.
*H01J 49/00* (2006.01)
*G01N 27/62* (2021.01)
*H01J 49/16* (2006.01)

(52) U.S. Cl.
CPC .......... *H01J 49/0036* (2013.01); *G01N 27/62* (2013.01); *H01J 49/164* (2013.01)

(58) Field of Classification Search
CPC .... H01J 49/0036; H01J 49/164; G01N 27/62; G16C 20/20
(Continued)

(56) References Cited

U.S. PATENT DOCUMENTS 9,159,538 B1* 10/2015 McClure ............... H01J 49/26
2015/0380225 A1* 12/2015 Yamada ............ H01J 49/0036
702/26

FOREIGN PATENT DOCUMENTS

CN 102221589 A 10/2011
WO 2014/128912 A1 8/2014

OTHER PUBLICATIONS

Communication dated Jun. 3, 2020, from the European Patent Office in application No. 16915165.1.
(Continued)

*Primary Examiner* — Michael Maskell
(74) *Attorney, Agent, or Firm* — Sughrue Mion, PLLC

(57) ABSTRACT

The compound list stored in identification information memory is populated with theoretical masses associated with a variety of compounds, as well as information such as the type of matrix capable of detecting said compound, potential neutral loss, etc. The adduct ion list, meanwhile, is populated with theoretical masses associated with a variety of adduct ions, as well as other information such as types of matrices capable of producing adducts, etc. When a user specifies a peak on the mass spectrum for a compound search, compound candidate search portion extracts combination candidates based on how well the measured m/z value of the specified peak matches the m/z value for combinations of compounds in the compound list and adduct ions in the adduct ion list, while the type of matrix used during measurement serves as a condition to narrow down the combinations. Display processing portion displays a list of the search results.

9 Claims, 9 Drawing Sheets

(58) Field of Classification Search
USPC .............................. 250/281, 282; 702/27, 28
See application file for complete search history.

(56) References Cited

OTHER PUBLICATIONS

Draper, John et al: "Metabolite signal identification in accurate mass metabolomics data with MZedDB, an interactive m/z annotation tool utilizing predicted ionisation behaviour 'rules'", BMC Bioinformatics, Biomed Central, London, GB, vol. 10, No. 227, Jul. 21, 2009, (Jul. 21, 2009), , XP021055673, ISSN: 1471-2105, DOI: 10.1186/1471-2105/10/227 ( 16 pages total).
"HMDB Human Metabolome Database," [online], The Metabolomics Innovation Centre, [searched Aug. 15, 2016], 4 pages.
International Search Report for PCT/JP2016/075724 dated Nov. 29, 2016 [PCT/ISA/210].
Written Opinion for PCT/JP2016/075724 dated Nov. 29, 2016 [PCT/ISA/237].
Communication dated Nov. 18, 2020 from The State Intellectual Property Office of the P.R. of China in Application No. 201680088956.9.

\* cited by examiner

Sample information input screen   ✕

Sample ID: test 4 SSD
Filename: D:¥KBMS¥KBMS-ITTOF|data

| Sample information 1 | Sample information 2 |

Preparation method: Spray ▼
Matrix type: DHB ▼
Comments:

BACK    END    CANCEL

FIG. 4A

Sample information input screen   ✕

Sample ID: test 4 SSD
Filename: D:¥KBMS¥KBMS-ITTOF|data

| Sample information 1 | Sample information 2 |

Collection data: ▼
Type of animal: Human ▼
Age: ▼
Sex: ▼
Organ: Liver ▼
Cell: Cancer cell ▼

BACK    END    CANCEL

FIG. 4B

| Compound | Compositional formula | Matrix | Ion polarity | Monoisotopic mass | Matrix origin | MS/MS library | Neutral loss mass | Neutral loss composition | Multimer |
|---|---|---|---|---|---|---|---|---|---|
| Lys(L-lysine) | C6H14N2O2 | 9-AA | Negative | 146.10552770 | 0 | 1 | | | |
| Lys(L-lysine) | C6H14N2O2 | CHCA | Positive | 146.10552770 | 0 | 1 | 18.01056468 | H2O | |
| Lys(L-lysine) | C6H14N2O2 | CHCA | Positive | 146.10552770 | 0 | 0 | | | |
| Lys(L-lysine) | C6H14N2O2 | DHB | Positive | 146.10552770 | 0 | 1 | 18.01056468 | H2O | |
| Lys(L-lysine) | C6H14N2O2 | DHB | Positive | 146.10552770 | 0 | 0 | 62.00039392 | CO2+H2O | |
| Lys(L-lysine) | C6H14N2O2 | DHB | Positive | 146.10552770 | 0 | 0 | | | |
| Glu(Glutamic acid) | C5H9NO4 | 9-AA | Negative | 147.05315780 | 0 | 1 | | | |
| Glu(Glutamic acid) | C5H9NO4 | CHCA | Positive | 147.05315780 | 0 | 1 | 18.01056468 | H2O | |
| Glu(Glutamic acid) | C5H9NO4 | CHCA | Positive | 147.05315780 | 0 | 0 | | | |
| Glu(Glutamic acid) | C5H9NO4 | DHB | Positive | 147.05315780 | 0 | 1 | 18.01056468 | H2O | |
| Glu(Glutamic acid) | C5H9NO4 | DHB | Positive | 147.05315780 | 0 | 0 | | | |
| Glu(Glutamic acid) | C5H9NO4 | DHB | Positive | 147.05315780 | 0 | 0 | | | |
| O-acetylserine | C5H9NO4 | 9-AA | Negative | 147.05316000 | 0 | 0 | | | |
| O-acetylserine | C5H9NO4 | CHCA | Positive | 147.05316000 | 0 | 0 | | | |
| O-acetylserine | C5H9NO4 | DHB | Positive | 147.05316000 | 0 | 0 | | | |
| (R)-(-)-citramalic acid | C5H8O5 | 9-AA | Negative | 148.03717340 | 0 | 0 | | | |
| (R)-(-)-citramalic acid | C5H8O5 | CHCA | Positive | 148.03717340 | 0 | 0 | | | |
| (R)-(-)-citramalic acid | C5H8O5 | DHB | Positive | 148.03717340 | 0 | 0 | | | |
| DL-a-hydroxyglutaric acid | C5H8O5 | 9-AA | Negative | 148.03717340 | 0 | 0 | | | |
| DL-a-hydroxyglutaric acid | C5H8O5 | CHCA | Positive | 148.03717340 | 0 | 0 | | | |
| DL-a-hydroxyglutaric acid | C5H8O5 | DHB | Positive | 148.03717340 | 0 | 0 | | | |
| trans-cinnamic acid | C9H8O2 | 9-AA | Negative | 148.05243000 | 0 | 0 | | | |
| trans-cinnamic acid | C9H8O2 | CHCA | Positive | 148.05243000 | 0 | 0 | | | |
| trans-cinnamic acid | C9H8O2 | DHB | Positive | 148.05243000 | 0 | 0 | | | |
| Mevalonate(3,5- dihydroxy-3-methylpentan... | C6H12O4 | 9-AA | Negative | 148.07355890 | 0 | 0 | | | |
| Guanine | C5H5N5O | CHCA | Positive | 151.04940980 | 0 | 1 | 17.02654910 | NH3 | |
| Guanine(2-aminohypoxanthine) | C5H5N5O | DHB | Positive | 151.04940980 | 0 | 1 | | | |
| Guanine(2-aminohypoxanthine) | C5H5N5O | 9-AA | Negative | 151.04940980 | 0 | 1 | | | |
| Xanthine | C5H4N4O2 | CHCA | Positive | 152.03342540 | 0 | 1 | 36.02112936 | 2(H2O) | |
| Xanthine(xanthine) | C5H4N4O2 | DHB | Positive | 152.03342540 | 0 | 1 | | | |
| Xanthine(xanthine) | C5H4N4O2 | DHB | Positive | 152.03342540 | 0 | 0 | | | |
| Xanthine(xanthine) | C5H4N4O2 | 9-AA | Negative | 152.03342540 | 0 | 0 | | | |
| 3-hydroxyphenylacetate | C8H8O3 | CHCA | Positive | 152.04734000 | 0 | 0 | | | |
| 3-hydroxyphenylacetate | C8H8O3 | DHB | Positive | 152.04734000 | 0 | 0 | | | |
| 3-hydroxyphenylacetate | C8H8O3 | 9-AA | Negative | 152.04734000 | 0 | 0 | | | |
| 4-hydroxyphenylacetate | C8H8O3 | CHCA | Positive | 152.04734000 | 0 | 0 | | | |
| 4-hydroxyphenylacetate | C8H8O3 | DHB | Positive | 152.04734000 | 0 | 0 | | | |
| 4-hydroxyphenylacetate | C8H8O3 | 9-AA | Negative | 152.04734000 | 0 | 0 | | | |

Positive adduct ions

| Adduct ion | Monoisotopic mass | Use | Matrix | Adduct |
|---|---|---|---|---|
| +H | 1.007276 | ✓ | | |
| +Na | 22.98922 | ✓ | | |
| +K | 38.96371 | ✓ | | |
| -e | -0.00054858 | ✓ | | |
| -H+2Na | 44.97116 | ✓ | | |
| -H+2K | 76.91904 | ✓ | | |
| -H+K+Na | 60.94510 | ✓ | | |
| -2H+3Na | 66.95311 | ✓ | | |
| -2H+3K | 114.8749 | ✓ | | |
| +DHB-H2O+H | 137.0233 | ✓ | DHB | 0 |
| +DHB-H2O+Na | 159.0053 | ✓ | DHB | 0 |
| +DHB-H2O+K | 174.9792 | ✓ | DHB | 0 |
| +2DHB-2(H2O)+H | 273.0394 | ✓ | DHB | 0 |
| +2DHB-2(H2O)+Na | 295.0213 | ✓ | DHB | 0 |
| +2DHB-2(H2O)+K | 310.9952 | ✓ | DHB | 0 |
| +3DHB-3(H2O)+H | 409.0554 | ✓ | DHB | 0 |

(b)

Negative adduct ions

| Adduct ion | Monoisotopic mass | Use | Matrix | Adduct |
|---|---|---|---|---|
| -H | -1.007276 | ✓ | | |
| +Cl | 34.96940 | ✓ | | |
| +e | 0.00054858 | ✓ | | |
| -2H+Na | 20.97467 | ✓ | | |
| -3H+2Na | 42.95661 | ✓ | | |
| -2H+K | 36.94860 | ✓ | | |
| -3H+2K | 74.90449 | ✓ | | |
| -3H+Na+K | 58.93055 | ✓ | | |
| -3H-2e | -3.024024 | ✓ | 9-AA | 1 |
| +9-AA+H | 193.0771 | ✓ | 9-AA | 0 |

FIG. 6

Imaging MS Solution Compound Search

Adduct Ion  Matrix  Compounds m/z: 192.00000000   Ion polarity: -   m/z Tolerance: 1.00000000 Da   Matrix Type: 9-AA   [Search]   26 candidate(s)

| # | Mass | Difference | Compound | Compositional formula | Adduction |
|---|------|------------|----------|----------------------|-----------|
| 1 | 191.98346761 | -0.01653239 | 5-aminovalerate | C5H11NO2 | M-3H+2K |
| 2 | 191.98346621 | -0.01653379 | Valine(L-valine) | C5H11NO2 | M-3H+2K |
| 3 | 192.01807727 | 0.01807727 | His(L-histidine) | C6H9N3O2 | M-2H+K |
| 4 | 192.01808077 | 0.01808077 | histidine | C6H9N3O2 | M-2H+K |
| 5 | 192.02755118 | 0.02755118 | citric acid(2-hydroxypropane-1,2,3-tricarboxyli... | C6H8O7 | M+e |
| 6 | 192.02755118 | 0.02755118 | isocitrate | C6H8O7 | M+e |
| 7 | 191.96805732 | -0.03194268 | Asp(L-aspartic acid) | C4H7NO4 | M-3H+Na+K |
| 8 | 192.04328850 | 0.04328850 | N-acetylproline | C7H11NO3 | M+Cl |
| 9 | 192.04438988 | 0.04438988 | 9-AA (9-aminoacridine) | C13H10N2 | M+H2O-NH3-3... |
| 10 | 191.94707761 | -0.05292239 | N-acetylproline | C4H7NO3 | M-3H+2K |
| 11 | 192.06393858 | 0.06393858 | D-(-)-Quinic acid | C7H12O6 | M+e |
| 12 | 192.06661394 | 0.06661394 | phenylacetylglycine | C10H11NO3 | M-H |
| 13 | 192.93109631 | 0.93109631 | Succinate(succinic acid) | C4H6O4 | M-3H+2K |
| 14 | 192.93243371 | 0.93243371 | Adenine(vitamin B4(Adenine)) | C5H5O5 | M-NH3+3H+2K |
| 15 | 192.93243373 | 0.93243373 | Hypoxanthine (6-hydroxypurine) | C5H4N4O | M-H2O+3H+2K |
| 16 | 191.06215858 | -0.93784142 | N-acetylmethionine | C7H13NO3S | M+e |
| 17 | 191.06037429 | -0.93962571 | 9-AA (9-aminoacridine) | C13H10N2 | M-3H-2e |
| 18 | 191.05878858 | -0.94121142 | 5-hydroxyinoacridine | C10H9NO3 | M+e |
| 19 | 191.05611394 | -0.94388606 | D-(-)-Quinic acid | C7H12O6 | M-H |
| 20 | 192.95207292 | 0.95207292 | Malate(2S)-2-hydroxybutanedioic acid) | C4H6O5 | M-3H+Na+K |
| 21 | 192.96747761 | 0.96747761 | beta-hydroxyisovalerate | C5H10O3 | M-3H+2K |
| 22 | 191.03017053 | -0.96982947 | Mevalonate(3,5-dihyroxy-3-methylpentanoic... | C6H12O4 | M-3H+2Na |
| 23 | 191.01972654 | -0.98027346 | citric acid(2-hydroxypropane-1,2,3-tricarboxyli... | C6H8O7 | M-H |

FIG. 7

MASS SPECTROMETRY DATA PROCESSING DEVICE

This is a National Stage of Application No. PCT/JP2016/075724, filed Sep. 1, 2016, the entire disclosure of which is hereby incorporated by reference.

TECHNICAL FIELD

The present invention relates to a mass spectrometry data processing device for processing of data obtained by performing mass spectrometry, and more specifically, relates to a mass spectrometry data processing device that processes data obtained by performing mass spectrometry of a sample in order to identify components (compounds) contained in said sample.

BACKGROUND ART

One known method of identifying an unknown compound using mass spectrometry is to find the mass-to-charge ratio of peaks surmised to correspond to said unknown compound on the mass spectrum obtained by performing mass spectrometry of a sample containing said unknown compound, and then to perform a library search using this mass-to-charge ratio as the search key. However, typically, it is very rare for a sample to contain only the unknown compound one seeks to identify. Usually, a sample containing the unknown compound will also contain other compounds. Hence, to identify an unknown compound by a library search, a sample would first be introduced into a liquid chromatography (LC) or capillary electrophoresis (CE) device or the like to separate the target unknown compound from the other compounds, and then be introduced into a mass spectrometer. Although techniques such as LC and the like do not necessarily completely separate an unknown compound from other compounds, they do eliminate overlap between the unknown compound and other compounds, considerably ameliorating the accuracy of an identification of an unknown compound obtained by a library search.

However, even if a mass spectrum can be obtained by separating the target unknown compound using LC or the like and performing mass spectrometry, in many cases it is challenging to locate peaks for simple proton adduct ions or proton loss ions originating from the unknown compound.

For example, if the sample is of biological origin, ionization is frequently performed by a technique such as electro spray ionization (ESI) or matrix-assisted laser desorption/ionization (MALDI). However, using an ionization method such as this occasionally results in the appearance of peaks of ionic origin on the mass spectrum due to the adduction of biologically abundant sodium (Na) ions or potassium (K) ions to the compound instead of protons, or the adduction of combinations thereof such as −H+2K, −H+2Na, −H+Na+K (where −H signifies loss of a proton and +2Na and +2K signify adduction of two Na ions or K ions).

Furthermore, using MALDI can cause multiple peaks originating from the used matrix to appear on the mass spectrum.

Specifically, peaks can appear on the mass spectrum corresponding to not only molecular ions of the matrix but also to H, K, Na, etc. ion adducts of said molecule, a variety of clusters (#multimers) of matrix molecules, or a variety of neutral-loss products thereof. Furthermore, ion peaks may also appear for matrix molecule adducts of compounds contained in the sample, protonated products thereof, or loss of $H_2O$ therefrom as neutral loss.

Furthermore, when target compound molecules are ionized, part of the structure of said molecule (H2O, etc.) may in some instances be lost during ionization. In the event of a neutral loss such as this, the peaks originating from this compound will appear on the mass spectrum displaced from the original mass-to-charge ratio of the compound in proportion to the mass of the lost molecule (e.g. H2O). Additionally, ionization may in some instances occur while multiple molecules of the target compound are in multimeric form, in which case the integral multiple of the mass of the molecule plus the mass of the H or other adduct ion will become the mass-to-charge ratio of the peak on the mass spectrum. It is also possible for ions produced by neutral loss from these multimers to show up on the mass spectrum.

Thus, when molecules of a target compound are ionized, it is common to observe multiple different peaks on the mass spectrum for adduct ions, neutral loss, and multimers, even though these all originate from the same molecule. Generally speaking, it is challenging to identify a compound by using the mass-to-charge ratios of such peaks to search a library of mass-to-charge ratio values of numerous compounds.

The Human Metabolome Database (HMDB) disclosed in Non-Patent Literature 1 is a well-known example of a general-purpose database of biogenic compounds such as metabolites. Using this database together with its associated compound search system, a user inputs a mass-to-charge ratio for a peak observed on a measured mass spectrum, and the system displays all combinations of compound molecules and adduct ions within the database with a matching mass, within a pre-determined margin of error. However, a problem with the aforesaid search system is that, in many cases, it is challenging to identify the target compound from among the numerous candidates displayed. Another problem is that, although the HMDB does contain Na and other adduct ions, it does not contain actual matrix molecules or adduct ions produced by adduction of matrix molecules to compounds in the sample, making it challenging to accurately identify which of the peaks observed on the mass spectrum originated from the matrix or were produced by adduction of the matrix to the sample molecules.

Meanwhile, in recent years, imaging mass spectrometers for investigating the spatial distribution, etc. of designated compounds within biological tissue have come to be used. However, imaging mass spectrometry is frequently performed by coating or spraying a matrix onto the surface of a sample, in the form of a slice of biological tissue or the like, and then immediately ionizing by MALDI and performing mass spectrometry.

In this case, unlike when the compounds are separated in advance by the aforementioned LC, CE, or the like, ionization occurs without having separated the multiple compounds contained in the sample, causing peaks originating from these numerous compounds to appear in the mass spectrum. Furthermore, compounds with a different composition but very similar mass, or isomers with the same composition that differ only in structure, will be observed as overlapping peaks on a mass spectrum, or in other words as the same compound. Additionally, multiple peaks from different adduction ions, neutral loss, and multimers of the aforementioned designated compounds will also show up.

In cases such as this, where multiple peaks originating from multiple compounds are observed on a mass spectrum, it is nearly impossible to accurately identify the corresponding compound even after conducting a library search based on the mass-to-charge ratio of the peaks on the mass spectrum. Hence, in instances such as this, an identification method making use of a mass spectrum obtained by MS" analysis (where n is an integer greater than or equal to 2) is occasionally used (MS" spectrum). In short, tandem mass spectrometry (MS" analysis) is performed by selecting the precursor ions for peaks suspected to originate from the compound to be identified on the mass spectrum, yielding a mass spectrum for product ions (MS" spectrum). This MS" spectrum is then used to conduct a database search to locate compounds with a similar spectral pattern and thereby identify the target compound (see Patent Literature 1, etc.).

However, if ions originating from compounds other than the target compound happen to overlap with the peaks selected as precursor ions on the mass spectrum, peaks for product ions originating from multiple compounds will appear on the MS" spectrum. Thus, accurate identification was in some instances not possible even when conducting a conventional database search using this manner of peak information based on the MS" spectrum.

Furthermore, because the MSn spectrum is limited to compounds listed in a database, this means that compound identification will not be possible if MSn analysis is performed after selecting as the precursor ion an ion originating from a compound with an MSn spectrum not listed in a database. However, prior to selecting a precursor ion or conducting MSn analysis, a user has no way of knowing whether or not the database contains an MSn spectrum obtained from MSn analysis targeting a precursor ion, meaning that performing MSn analysis can in some cases be an unnecessary waste of time and effort.

PRIOR ART LITERATURE

Patent Literature (Patent literature 1) International Publication No. 2014/128912

Non-Patent Literature (Non-patent literature 1) "HMDB Human Metabolome Database," [online], The Metabolomics Innovation Centre, [searched Aug. 15, 2016], internet

SUMMARY OF THE INVENTION

Problem to be Solved by the Invention

The present invention was devised in view of the aforesaid problems, having as its primary objective to provide a mass spectrometry data processing device that is able to provide a user with information that accurately narrows down candidate compounds when extrapolating a target compound based on a mass spectrum on which it is possible to observe numerous adduct ions produced by adduction of other substances to the target compound, ions produced by neutral loss from the target compound, or ions of other substances such as the matrix itself.

Another objective of the present invention is to provide a mass spectrometry data processing device that is able to inform a user as to whether or not a selected precursor ion is appropriate for identification purposes prior to performing MSn analysis to identify a target compound.

Means of Solving the Problem

The present invention, which was devised to solve the aforesaid problems, is a mass spectrometry data processing device that identifies compounds contained in a sample based on mass spectrum data obtained by performing mass spectroscopy of said sample, characterized in that it is furnished with:

a) Compound information memory that stores the theoretical mass of a variety of compounds, and, when a compound is ionized under designated ionization conditions, also storing those ionization conditions together with the corresponding compound;

b) Adduct information memory that stores the theoretical mass of adduct ions adducted to a compound during ionization, correlated to the adduct ion, and, when adduction to a compound occurs under designated ionization conditions, also stores the ionization conditions correlated to the adduct ion;

c) Condition input portion for the user to input ionization conditions during mass spectrometry; and d) Compound candidate search portion that finds the measured mass-to-charge ratio of peaks to be identified on a mass spectrum obtained by mass spectrometry and, based on said measured mass-to-charge ratio and the ionization conditions input via the condition input portion, extracts compound and adduct ion combination candidates corresponding to the peaks from among combinations of adduct ions stored in the adduct information memory and compounds stored in the compound information memory.

Preferably, the mass spectrometry data processing device of the present invention is configured to further be furnished with a display processing portion that displays compound and adduct ion combination candidates obtained by searching with the compound candidate search portion.

Furthermore, the peaks to be identified can be specified by, for example, having a user make a selection by clicking on the mass spectrum, or by having a user read the mass-to-charge ratio of the target peak and input that number on a designated screen.

In the mass spectrometry data processing device of the present invention, adduct ions can be said to include one or more or multiple combinations of, for example, H ions (protons), Na ions, K ions, etc. Electrons, although not, strictly speaking, adduct ions, may be stored in the adduct information memory portion as adduct ions. If a mass spectrometer with a MALDI ion source is used as the mass spectrometer, the adduct information memory portion should also be made to include the following as adduct ions: molecular ions of a variety of matrices used in sample preparation, ions adducted with protons or alkaline metal ions, and adduct ions produced by loss of one or more water molecules ($H_2O$) from the same.

For example, if a mass spectrometer equipped with ion sources using a variety of ionization methods, e.g. ESI, MALDI, PESI (probe electrospray ionization), etc., is used as the mass spectrometer from which data is to be obtained, the variety of ionization method should be included as an ionization condition due to the fact that different ionization methods result in the adduction of different adduct ions to a compound. In contrast, if a mass spectrometer equipped with ion sources of a designated ionization method is used as the mass spectrometer from which data is to be obtained, the type of ionization method can be omitted from the ionization conditions, and elements other than this that may affect the type of adduct ion adducted to compounds can be included as ionization conditions.

For example, if using a mass spectrometer equipped with a MALDI ion source, a variety of ions originating from matrix molecules will become adduct ions, as described above. Hence, at the very least, the type of MALDI matrix would be included as an ionization condition, e.g. DHB (2,5-dihydroxybenzoic acid), CHCA (α-cyano-4-hydroxycinnamic acid), 9-AA (9-aminoacridine), etc.

If using a mass spectrometer equipped with an ESI or PESI ion source, the type of solvent (mobile phase in the case of a combination with a liquid chromatograph), etc. would be included as an ionization condition.

In the mass spectrometry data processing device of the present invention, the compound information memory portion stores not only compound names (and/or compositional formulae) correlated to their theoretical mass (the term theoretical mass used here is an exact mass value found by calculation), but also ionization conditions for each compound when there is a possibility of their being detected in a state in which adduct ions have been adducted. In contrast, the adduct information memory portion stores a variety of adduct ions together with their theoretical mass and ionization conditions. Note that the information stored in the compound information memory portion and the adduct information memory portion can either be created ahead of time by the manufacturer providing this device, or created afterwards by the user (after purchasing the device). Generally speaking, it is desirable for the manufacturer to create a basic set of information so that the user can add, remove, or edit information on an as-needed basis.

Either before performing mass spectrometry or after concluding mass spectrometry, a user inputs the ionization conditions via the condition input portion. For example, if a user specifies a peak they wish to identify on a mass spectrum obtained by mass spectrometry, the compound candidate search portion will find the measured mass-to-charge ratio of the specified peak. In prior-art general-purpose compound searches, candidate compounds were extracted by comparing this measured mass-to-charge ratio to the theoretical mass-to-charge ratio of each compound stored in the compound information memory. In contrast, in the mass spectrometry data processing device of the present invention, the compound candidate search portion compares the theoretical mass-to-charge ratio of a variety of combinations of compounds stored in the compound information memory and adduct ions stored in the adduct information memory to the measured mass-to-charge ratio, but excludes combinations that do not conform to the input ionization conditions.

For example, if DHB matrix is specified as an ionization condition, candidates are extracted that meet the requirement of being a combination of compounds detectable in this DHB matrix and adduct ions capable of being generated under a DHB matrix, and where the theoretical mass-to-charge ratio and measured mass-to-charge ratio of those combinations are a match within a designated margin of error. By this means, combinations containing compounds that would not be detected under a different matrix such as, for example, CHCA and adduct ions only generated under a different matrix would not be extracted even if the theoretical mass-to-charge ratio and measured mass-to-charge ratio of those combinations were a match. The display processing portion then displays the combinations that were found in list form, for example.

Note that, because ionization of the same compound can result in positive ions or negative ions depending on the compound, searching can be made more efficient by treating the same compound differently within the compound information memory portion depending on if its polarity is positive or negative, and by differentiating between adduct ions that generate positive ions and adduct ions that generate negative ions within the adduct information memory portion.

Furthermore, in the mass spectrometry data processing device of the present invention:

In the event that a designated adduct ion is adducted to a compound in a designated type of sample during ionization of said compound, the compound information memory stores the type of that sample associated with the compound, and the adduct information memory stores the type of that sample associated with the adduct ion;

The condition input portion enables input of the type of sample that is subject to mass spectrometry; and The compound candidate search portion can be configured so as to also use information about the type of sample input via the condition input portion to narrow down the results when extracting candidates for combinations of compounds and adduct ions corresponding to the peak.

If the sample is a slice of biological tissue collected from the organ of an animal, the type of sample can be, for example, the type of animal, the type of organ, the nature of the biological tissue (cancer cell, noncancer cell, etc.), etc. If the sample collected from an animal is a liquid, the type of the sample could be the type of animal, the type of liquid (blood, saliva, etc.), etc.

According to this configuration, it is possible to eliminate candidates containing compounds that should not be detected in a given type of sample under measurement, or containing adduct ions that should not be adducted, thereby making it possible to further narrow down the compound candidates presented to the user.

Furthermore, in the mass spectrometry data processing device of the present invention:

Information about neutral loss from a compound when said compound is ionized is also stored associated with that compound in the compound information memory; and The compound candidate search portion is preferably configured so as to use information on neutral loss stored in the compound information memory when extracting candidates for combinations of compounds and adduct ions corresponding to the peak.

Information about neutral loss here conventionally means the compositional formula for neutral loss and the theoretical mass thereof. For example, in amino acid and the like, $H_2O$ or $H_2O$ and $CO_2$ may in some instances be lost as neutral loss during ionization.

According to the configuration, if neutral loss information is associated with a compound stored in the compound information memory, once the mass of neutral loss is subtracted from the mass of the compound, it is relatively easy to calculate the mass of its combinations with adduct ions. This makes it possible to efficiently conduct searches for compound candidates, including neutral loss.

Furthermore, in the mass spectrometry data processing device of the present invention, The compound information memory stores information about the degree of polymerization of a multimer associated with a compound; and The compound candidate search portion is configured so as to use information about multimers stored in the compound information memory when extracting candidates for combinations of compounds and adduct ions corresponding to the peak.

Depending on the compound, multiple molecules may combine into a multimer (cluster) during ionization, either adding adduct ions to this multimer or incurring neutral loss. According to the configuration, such combinations of multimers and adduct ions as well as products of neutral loss from multimers are also included in the compound search, which makes it possible to more accurately and exhaustively provide the user with compound candidates matching the peak identified by the user.

Furthermore, if a mass spectrometer equipped with a MALDI ion source is used as the mass spectrometer, the mass spectrometry data processing device of the present invention can be configured such that:

The adduct information memory stores identifier information associated with adduct ions indicating whether or not these are adducted to the matrix molecule itself;

The compound information memory stores identifier information associated with the compound indicating whether it is a matrix molecule or multimer thereof; and The compound candidate search portion uses the identifier information stored in the adduct information memory and the compound information memory when extracting candidates for combinations of compounds and ions matching the peak.

According to this configuration, the matrix molecule itself, for example, is stored in the compound information memory, so even if an adduct ion containing the same matrix molecule is stored in the adduct information memory, appropriately setting the identifier information makes it possible to avoid compounds with essentially the same composition from being redundantly chosen as candidates.

Furthermore, in the mass spectrometry data processing device of the present invention, preferably:

A spectrum library is furnished for storing MSn spectra associated with compounds;

The compound information memory stores information indicating whether or not MSn spectra are present in the spectrum library, associated with compounds; and The display processing portion is configured so as to display search results in a format that renders it possible to visually determine whether or not an MSn spectrum corresponding to a combination of compound and adduct obtained by searching with the compound candidate search portion is present in the spectrum library.

Specifically, this can be done by displaying combinations of compound and adduct ion whose MSn spectrum is present in the spectrum library in a format or color (e.g. bold, italic, etc.) that sets it apart from other combinations for which this is not the case. If a large number of compound candidates appear in the compound search results, it is preferable to perform MS2 analysis of the target peak to be identified, and to perform a library search using its MS2 spectrum, but a library search will be a waste of time if the spectrum library does not contain that compound candidate's MS2 spectrum. With the configuration, in contrast, the user is immediately able to see whether or not the MS2 spectrum of a compound listed as corresponding to the peak specified by the user as the target for identification is present in the spectrum library. This enables the user to know whether or not there is any point in performing a library search using the MS2 spectrum prior to performing MS2 analysis or performing a library search.

Furthermore, in the mass spectrometry data processing device of the present invention:

A configuration can be adopted that is additionally furnished with a spectrum display processing portion that displays the mass spectrum obtained by mass spectrometry on a display screen superimposed with information indicating the standard peak width calculated theoretically based on a pre-set mass resolution and the mass-to-charge ratio of the indicated peak.

Particularly in the case of imaging mass spectrometry and the like, subjecting a sample directly to mass spectrometry without first separating the components by LC or CE often results in peaks originating from different compounds overlapping on the mass spectrum. If several peaks overlap with only a slight displacement (not separated enough to prevent their clear identification as multiple peaks), their peak width can be wider than the standard peak width. For this reason, when a user attempts to specify a peak to be identified on a mass spectrum, for example, the width of the peak on the mass spectrum can be compared with the superimposed information showing the standard peak width, making it easy to visually determine whether or not that peak originates from a single compound or is a combination of several overlapping peaks.

Effect of the Invention

According to the mass spectrometry data processing device of the present invention, when searching for candidates for compounds corresponding to a peak on a mass spectrum based on the mass-to-charge ratio of said peak, candidates with no chance of being observed are excluded, making it possible to provide the user with candidates for compounds and adduct ions accurately and with high precision.

Furthermore, the user is able to know if the peak specified by the user on the mass spectrum is unrelated to the compound in the sample, e.g. is a peak originating from a matrix molecule, making it possible to avoid performing MS2 analysis targeting that peak, for example, thereby eliminating unnecessary work and making it possible to carry out compound identification work more efficiently.

Furthermore, according to a configuration that explicitly displays whether or not an MSn spectrum is present in the spectrum library for candidate combinations of compounds and adduct ions found as a result of a compound search, it is possible to know whether or not performing MSn analysis will prove useful prior to doing so, making it possible to avoid unnecessarily performing MSn analysis.

BRIEF DESCRIPTION OF THE DRAWINGS

FIG. 4A and FIG. 4B Diagram showing an example of the sample information input screen in the mass spectroscopy system in this embodiment example.

FIG. 5 Diagram showing an example of a compound list in the mass spectroscopy system in this embodiment example.

FIG. 6 Diagram showing an example of the adduct ion list in the mass spectroscopy system in this embodiment example.

FIG. 7 Diagram showing an example of the compound search results in the mass spectroscopy system in this embodiment example.

EMBODIMENT OF THE INVENTION

An embodiment example of a mass spectroscopy system using the mass spectroscopy data processing device of the present invention will be described below referencing the annexed drawings.

Figure 1:
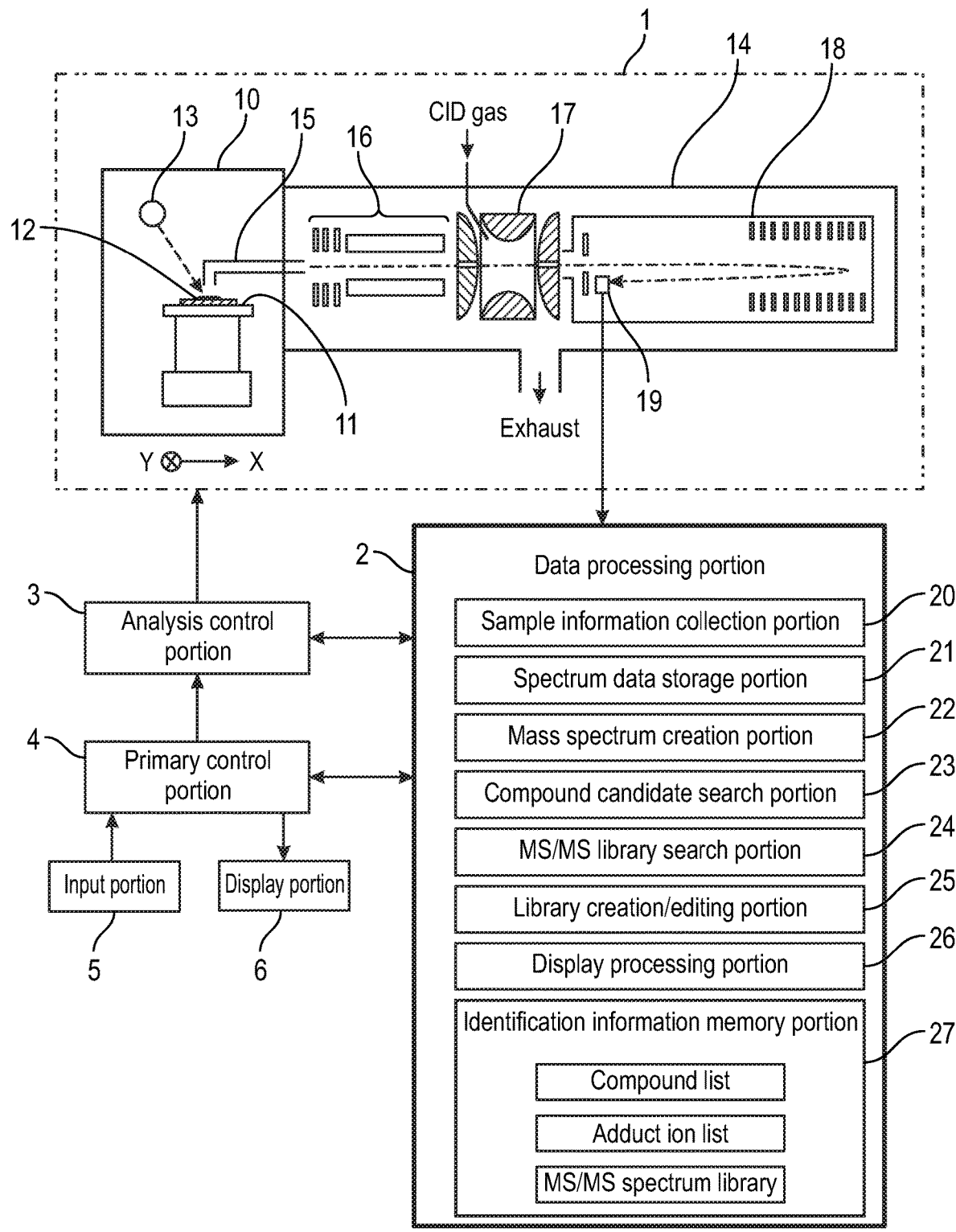
FIG. 1 Schematic view of one embodiment example of a mass spectroscopy system using the mass spectroscopy data processing device of the present invention.

FIG. 1 is a schematic diagram of the mass spectroscopy system in this embodiment example.

The mass spectroscopy system in this embodiment example is an imaging mass spectroscopy system that performs mass spectroscopy for each of a plurality of measurement points within a two-dimensional region on the sample and, based on data obtained thereby, is able to create an image showing the signal strength distribution of a designated mass-to-charge ratio within the two-dimensional region.

The mass spectroscopy system in this embodiment example is furnished with a measurement portion 1 that performs mass spectroscopy of a sample, data processing portion 2 that performs the below-described data processing of data obtained by measurement portion 1, analysis control portion 3 that controls each component of measurement portion 1, primary control portion 4 that controls the system as a whole as well as handling the user interface, input portion 5 operated by the user (analyst), and display portion 6 that displays analysis results, etc.

Measurement portion 1 is a MALDI-ion trap-time of flight mass spectrometry (MALDI-IT-TOFMS) device capable of performing MSn analysis of measurement points (microregions) at different locations on sample 12. In short, measurement portion 1 incorporates a sample stage 11 capable of moving along two mutually orthogonal axes X and Y installed in an ionization chamber 10 having an atmospheric pressure atmosphere; laser irradiation portion 13 that ionizes components in sample 12 by irradiating said sample 12 on sample stage 11 with laser light stopped down to a microdiameter; ion introduction portion 15 that collects ions produced by sample 12 and transports them into a vacuum chamber 14 maintained at a vacuum atmosphere; ion guide 16 that guides and converges ions originating from sample 12; ion trap 17 that temporarily captures ions by means of a high-frequency quadrupole field and, if necessary, selects precursor ions and performs dissociation of said precursor ions (collision-induced dissociation or CID); flight tube 18 that internally forms a flight space that separates ions emitted from said ion trap 17 according to the mass-to-charge ratio; and detector 19 that detects ions. However, as described below, the configuration of measurement portion 1 is not limited thereto, and can be altered variously.

Data processing portion 2 is furnished with a sample information collection portion 20, spectrum data storage portion 21, mass spectrum creation portion 22, compound candidate search portion 23, MS/MS library search portion 24, library creation/editing portion 25, display processing portion 26, identification information memory portion 27, etc., as the functional block that characterizes the mass spectrometry system in this embodiment example. Stored in identification information memory portion 27 is a compound list, adduct ion list, and MS/MS spectrum library. The compound list and adduct ion list will be described below. The MS/MS spectrum library is a library that contains the MS/MS spectra (product ion spectra) of a variety of compounds in a form associated with those compounds. Note that the compound list, adduct ion list, and MS/MS spectrum library can be collated into a single file, or can be separate files, and the file structure thereof can be determined at will.

Furthermore, part of data processing portion 2, primary control portion 4, and analysis control portion 3 can be hardware resources in a personal computer (or high-performance workstation) such as CPU, RAM, ROM, etc., such that the function of each is implemented on said computer by running specialized control/processing software installed on said computer.

The sequence of operations for performing imaging mass spectroscopy of a sample such as a slice of biological tissue with the mass spectroscopy system in this embodiment example will be described schematically below.

Sample 12 is prepared by placing the sample to be measured on a MALDI sample plate and applying (or spraying) an appropriate matrix onto the surface of this sample. The user sets the prepared sample 12 onto sample stage 11 and, referencing the optical image obtained prior to the application of a matrix by a photography portion not shown in the drawings, specifies the region of interest on sample 12 that is to be observed. The user then enters a variety of analysis conditions via input portion 5, and specifies the measurement time.

In this system, it is possible to input sample information as an analysis condition. In short, performing a designated operation on input portion 5 causes a sample information input screen of the kind shown in FIG. 4A to be displayed on the screen of display portion 6. FIGS. 4A and B are tab-switchable screens. Here, in the "Sample Information 1" tab shown in FIG. 4A, the user selects or inputs the type of matrix and how the matrix is applied onto the sample (preparation method). In this example, "DHB" has been selected as the type of matrix and "Application" has been selected as the preparation method. In the "Sample Information 2" tab shown in FIG. 4A, the user selects or inputs the type of animal, type of organ, nature of the cell, etc. as sample type information. In this example, "human" has been selected as the type of animal, "liver" has been selected as the type of organ, and "cancer cell" has been selected as the nature of the cell. Note that it is not necessary to input each item in "Sample Information 1" and "Sample Information 2," but doing so helps to better narrow down the candidates returned via the below-described compound search.

Upon being instructed to start measurement, analysis control portion 3 performs mass spectroscopy of sample 12 by controlling each component of measuring portion 1. In short, first, sample stage 11 is moved to a designated position, and microdiameter laser light is emitted by laser irradiation portion 13, irradiating sample 12 on sample stage 11. Compounds present at the location where the laser light impacts sample 12 are ionized. The generated ions are transported into vacuum chamber 14 via ion introduction portion 15, and then converged by ion guide 16 and introduced into ion trap 17, where they are temporarily retained by the action of the quadrupole field.

These various ions are emitted from ion trap 17 at a designated timing, whereupon they are introduced into a flight space within flight tube 18, flying through said flight space until they reach detector 19.

While flying through the flight space, each type of ion is separated according to its mass-to-charge ratio, reaching detector 19 in order from those with a smaller to a larger mass-to-charge ratio. After the analog detection signal of detector 19 is converted to digital data by an analog-digital converter not shown in the drawings, it is input to data processing portion 2, where the flight time is converted to a mass-to-charge ratio and stored in spectrum data storage portion 21 as mass spectrum data.

Every time that mass spectrum data is obtained for a single measurement point, sample stage 11 is moved appropriately in the X-axis direction and the Y-axis direction by a drive portion not shown in the drawings. By thus changing the location where laser light impacts sample 12, and repeatedly moving sample stage 11 and emitting pulsed laser light, mass spectroscopy is performed for multiple measurement points within the region of interest on sample 12, and mass spectrum data for each of these multiple measurement points is stored in spectrum data storage portion 21. Sample information collection portion 20 obtains information input via the sample information input screen shown in FIG. 4A and FIG. 4B, i.e. sample information pertaining to the type of matrix, type of sample, etc., and stores this sample information together with the data in the same file or in a separate file but mutually associated.

Next is a description of the data processing that is characteristic of this system when identifying compounds contained in sample 12 based on mass spectrum data for multiple measurement points stored in spectrum data storage portion 21 in the manner described above.

Figure 2:
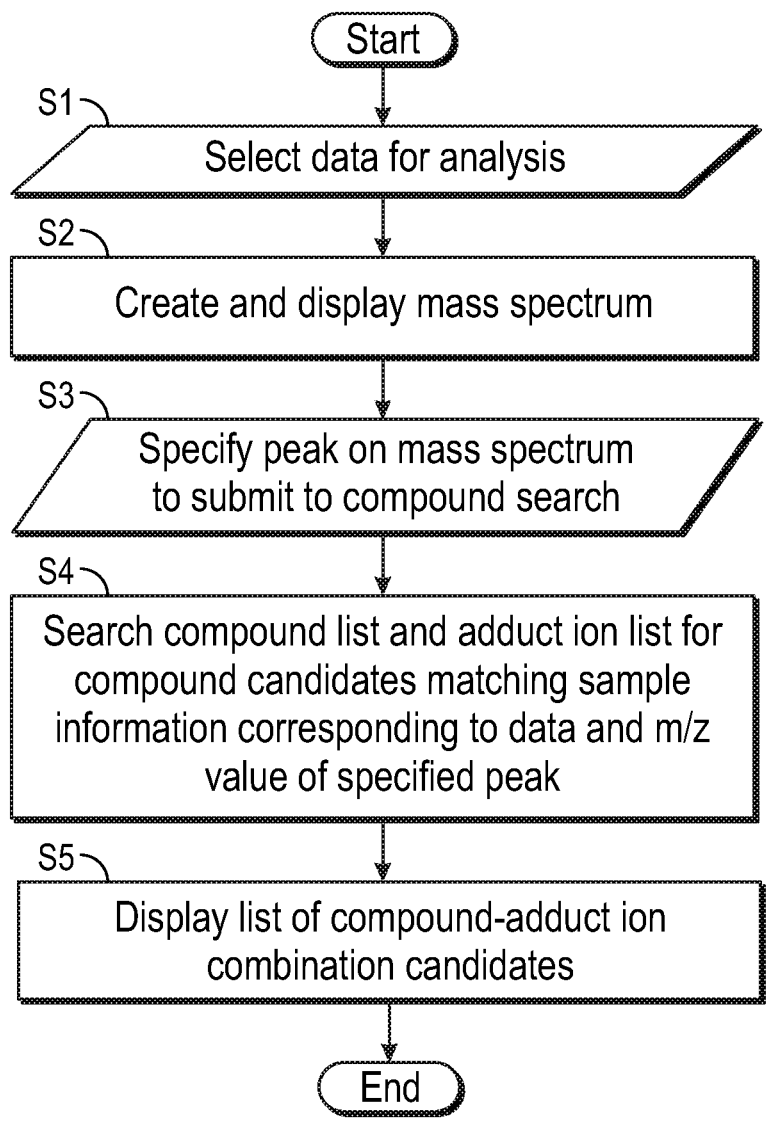
FIG. 2 Flowchart of characteristic data processing during identification of chemicals in a sample in the mass spectroscopy system in this embodiment example.
Figure 3:
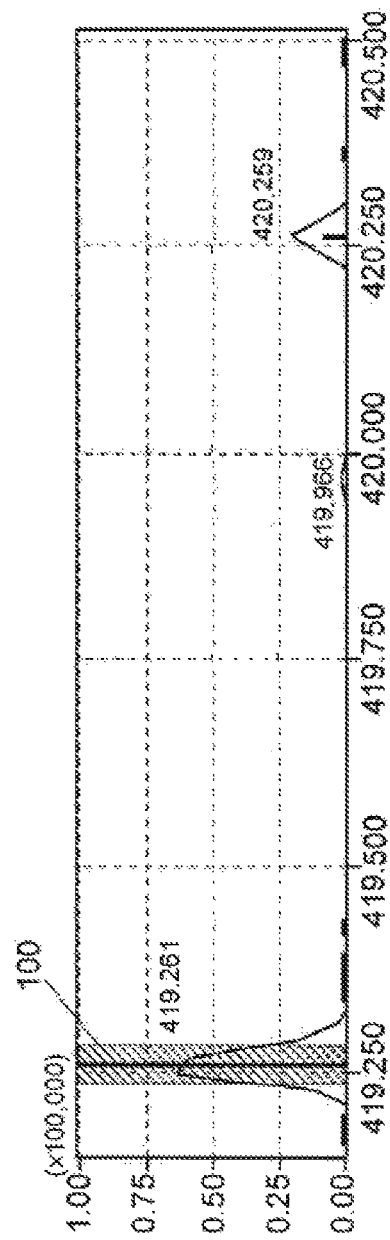
FIG. 3 Diagram showing an example of the mass spectrum display screen shown during a chemical search with the mass spectroscopy system in this embodiment example.

FIG. 2 is a flowchart of the process of compound estimation based on mass spectrum data. FIG. 3 is a diagram showing an example of the mass spectrum display screen, FIG. 5 is a diagram showing an example of the compound list, FIG. 6 is a diagram showing an example of the adduct ion list, and FIG. 7 is a diagram showing an example of the compound search results.

First, using FIG. 5 and FIG. 6, the compound list and adduct ion list saved in identification information memory portion 27 and used to perform the below-described compound search are described.

As shown in FIG. 5, the compound list is able to accommodate entry of information in a variety of fields associated with the name of each compound, including "Compositional formula," "Matrix," "Ion polarity," "Monoisotopic mass," "Matrix origin" identification flag, "MS/MS library" registration flag, "Neutral loss mass," "Neutral loss composition," "Multimer," etc.

"Matrix" is the type of matrix in which that compound can be detected. "Monoisotopic mass" is a theoretical mass value obtained by theoretical calculation. "Matrix origin" identification flag is a flag indicating whether or not the compound in question is of matrix origin.

Here, this value is set to "1" or "2" if the compound is a matrix molecule, matrix multimer, or a designated neutral loss from these molecules, but otherwise is set to "0." "MS/MS library" registration flag is a flag that indicates whether or not the MS/MS spectrum for that compound is registered in the MS/MS spectrum library in identification information memory portion 27. If yes, this value is set to "1"; if no, this value is set to "0." "Neutral loss mass" and "Neutral loss composition" are each set if neutral loss from that composition is possible. "Multimer" indicates the degree of polymerization if a multimer of polymerized matrix molecules is possible.

Each line of the compound list contains one combination of this set of fields. Accordingly, if the same compound can be detected by mass spectroscopy using multiple matrices, a separate line with the same compound name but a different matrix name is entered. The same applies in the case of neutral loss. For example, in the case of the amino acid Lys (L-lysine), a peak with no neutral loss is detected when using a DHB matrix, but an ionization peak is also present for loss of H2O or H2O and CO2 by neutral loss. When several types of neutral loss are present in this way, these are each recorded on a separate line. In the example in FIG. 5, lines 1 through 6 of the list are all for Lys (L-lysine). Furthermore, when DHB matrix is used, ionization peaks with several H2O missing from the multimer of the DHB matrix molecules can be observed in some instances, depending on the compound. In such instances, the "Multimer" field should be populated with information about the number of polymerizations of the multimer.

Furthermore, depending on factors such as the presence or absence of neutral loss and differences in matrix or ion polarity, even compounds with the same name in the compound list may differ in the pattern of their MS/MS spectrum (product ion spectrum) obtained by MS/MS analysis. For this reason, the value for the "MS/MS library" flag is set to "1" only when the fields for neutral loss, multimer degree of polymerization, ion polarity, and matrix type are a perfect match with the fields obtained from the product ion spectrum.

In contrast, as shown in FIG. 6, the adduct ion list is divided into list (a) for positive polarity adduct ions and list (b) for negative polarity adduct ions, with fields such as "Monomer isotopic mass," "Use," "Matrix," and "Adduct" setting flag being provided associated with the relevant adduct ion name (or compositional formula). "Use" is for setting whether or not that adduct ion is to be used in the compound search.

To not use it, the user unchecks the checkbox. "Matrix" signifies the type of matrix that can produce adduct ions thereof. A blank field means that the use of a designated matrix is not a condition. In other words, if the "Matrix" field is blank, all matrices of that adduct ion will be considered during a compound search. The "Adduct" setting flag indicates whether or not to include combinations with multimers of matrix molecules for consideration. This flag is set to "0" to ignore (not calculate) combinations of that adduct ion with matrix multimers and "1" to include such combinations. For reasons described below, this is typically best left as "0."

For example, in some instances when using a DHB matrix, molecules of the DHB matrix missing H2O can become adducted to the compound molecules of the sample, with a proton becoming adducted thereto. In such cases, as indicated on line 10 of the positive-polarity adduct ion list shown in FIG. 6 at (a), +DHB−H2O+H would be registered as an adduct ion, and DHB would be registered as a matrix for that adduct ion. In contrast, simple adduct ions such as +H and +Na can appear irrespective of the type of matrix used, so the limitation on the type of matrix is removed by leaving the matrix field blank.

Note that information indicating in what kind of sample a compound can be detected can also be included in the compound list. Here, sample type information refers to the same information that can be input or selected in the "Sample information 2" tab shown in FIG. 4B.

Although the compound list, adduct ion list, and MS/MS spectrum library would typically be stored in the identification information memory portion 27 created in advance by the manufacturer that supplies this system (in actuality, these are incorporated as part of the control/processing software), the user can use the functions of the library creation/editing portion 25 to create lists, add new compounds or adduct ions to an existing list, or to edit or delete existing content.

Next, the operating and processing sequence when performing a compound search will be described in accordance with FIG. 2.

The user performs a designated operation on input portion 5 to select the data they wish to analyze from among the data stored in spectrum data storage portion 21 (step S1). Upon receiving this select operation, mass spectrum creation portion 22 reads the relevant data from spectrum data storage portion 21 and creates a mass spectrum. Display processing portion 26 displays a mass spectrum on the screen of display portion 6 by way of primary control portion 4 (step S2).

Here, the mass spectrum data subject to analysis can correspond to a single measurement point within the region of interest, or can be an average mass spectrum of the entire region of interest, or multiple measurement points contained within a designated range thereof.

Once the user selects the peak for which they wish to conduct a compound search on the mass spectrum displayed on the screen, as shown in FIG. 3, the instruction to carry out the compound search based on the mass-to-charge ratio is provided by performing a designated operation (step S3). A peak can be selected by moving the cursor onto the target peak in the mass spectrum and clicking.

Upon receiving this instruction, compound candidate search portion 23 finds the mass-to-charge ratio of the center of mass of the selected peak as a measured m/z value. Subsequently, a determination is made as to whether or not the theoretical m/z value, which is obtained by totaling the theoretical mass of the various combinations of the compounds listed in the compound list and the adduct ions listed in the adduct ion list (monoisotopic mass), matches the measured m/z value within a designated margin of error. At this time, candidates for compound-adduct ion combinations are narrowed down by referencing the sample information (matrix type) appended to the data (step S4).

In short, if DHB matrix is specified as sample information, entries in the compound list are excluded if their "Matrix" field does not contain "DHB." Entries in the adduct ion list, too, are excluded unless the "Matrix" field contains "DHB" or is blank (no matrix restriction). Lines in the compound list that were not excluded, i.e. lines where the matrix is set to DHB, have a positive ion polarity, so the negative polarity adduction ion list is excluded. Combinations of the remaining compounds and adduct ions are then judged for how well their theoretical m/z value matches the measured m/z value. For compounds where neutral loss is specified, the theoretical m/z value for combinations of those compounds with adduct ions is compared to the measured m/z value after first subtracting the theoretical mass of the neutral loss from the theoretical mass of the compound. For compounds in which a degree of multimer polymerization is set (e.g. actual matrix molecules), the theoretical m/z value for combinations of those compounds with adduct ions is compared to the measured m/z value after multiplying the theoretical mass of that compound's molecule by the degree of polymerization.

The reason for setting the "Adduct" flag will be described below. Assume that the compound list includes DHB matrix molecules or DHB dimers minus H2O. At this time, if the adduct ion list contains +DHB−H2O+H, combinations of DHB molecules in the compound list and +DHB−H2O+H in the adduct ion list will have the same theoretical m/z value as combinations of DHB−H2O in the compound list and +H in the adduct list.

If this value matches the measured m/z value, both of those combination candidates will be extracted. However, in reality, these two combinations clearly represent the same ion. In short, simply adding matrix molecules to the compound list will in some instances result in overlapping combinations. To avoid this, the "Adduct" setting flag is used in the mass spectroscopy system in this embodiment example.

As described above, when the value of the "Adduct" setting flag is "0," combinations of that adduct ion with matrix multimers are ignored. The compound list also has the "Matrix origin" identification flag to determine whether or not a compound is a matrix molecule or multimer thereof. If the value is "1," combinations thereof with adduct ions in the adduct ion list where the "Adduct" setting flag's value is "0" will be ignored. This makes it possible to avoid extracting overlapping combinations of what are essentially the same ions, as described above.

In contrast, when using 9-AA as a matrix, situations may arise in which the adduct ion is −3H−2e. −3H indicates loss of three protons, while −2e indicates loss of two electrons, resulting in a monovalent negative ion. This manner of adduct ion originates from the molecular structure of 9-AA matrix, and is adducted only to 9-AA or multimers thereof. In these situations, −3H−2e would be added to the adduct ion list, and the "Adduct" setting flag's value would be set to "1." If the "Adduct" setting flag's value is "1," this means that the adduct ion is adducted only to the designated matrix molecule, and that hence only relevant compound-adduct ion combinations need be considered.

Note that, if an adduct ion is a polyvalent ion, the theoretical mass of a compound in the compound list could be added to the theoretical mass of the adduct ion before subtracting the valence of the ion from this value. Combinations in which the resultant m/z value and the measured m/z value match would then be extracted.

Once candidates for combinations of compounds and adduct ions in which the theoretical m/z value and measured m/z value match have been extracted in the manner described above, these candidates can be converted into a list by display processing portion 26 and displayed on the screen of display portion 6 by primary control portion 4 (step S5). In short, what is displayed at this point is candidates for combinations of compounds and adduct ions that correspond to the peak specified by the user in step S3. When creating a list of candidates for combinations of compounds and adduct ions, display processing portion 26 checks the "MS/MS library" registration flag corresponding to a given compound in the compound list. If the value of said flag is "1," i.e. if an MS/MS spectrum corresponding to this compound is registered in the MS/MS spectrum library, lines indicating this combination of compound and adduct ion in the candidate list are highlighted or displayed in a different color from the other lines.

Note that, at this time, the background display color is determined solely by the value of the "MS/MS library" registration flag corresponding to the compound, irrespective of the adduct ion, with no limit on possible combinations of adduct ions FIG. 7 shows an example of this display.

If there are multiple candidates for combinations of compounds and adduct ions, as shown in FIG. 7, one method of determining which of the candidates contains the true compound is to conduct an MS/MS library search. During an MS/MS library search, the MS/MS spectrum library is searched for MS/MS spectra that match the spectrum pattern of the MS/MS spectrum obtained by MS/MS analysis. If no matching MS/MS spectra are found in the MS/MS spectrum library, the user will have a very difficult time guessing the structure of the compound. If an MS/MS library search turns up no compounds, MS/MS analysis will have been a waste of time. In the system in this embodiment example, in contrast, candidates for combinations of compounds and adduct ions are displayed in the manner described above, which makes it possible to not only identify compound candidates corresponding to the specified peak on the mass spectrum, but also to determine whether or not the MS/MS spectra of those compound candidates are contained in the MS/MS spectrum library, i.e. if they can be found by a search of the MS/MS library. This makes it possible to avoid unnecessarily performing MS/MS analysis when doing so would not help in identifying the target compound.

Figure 9:
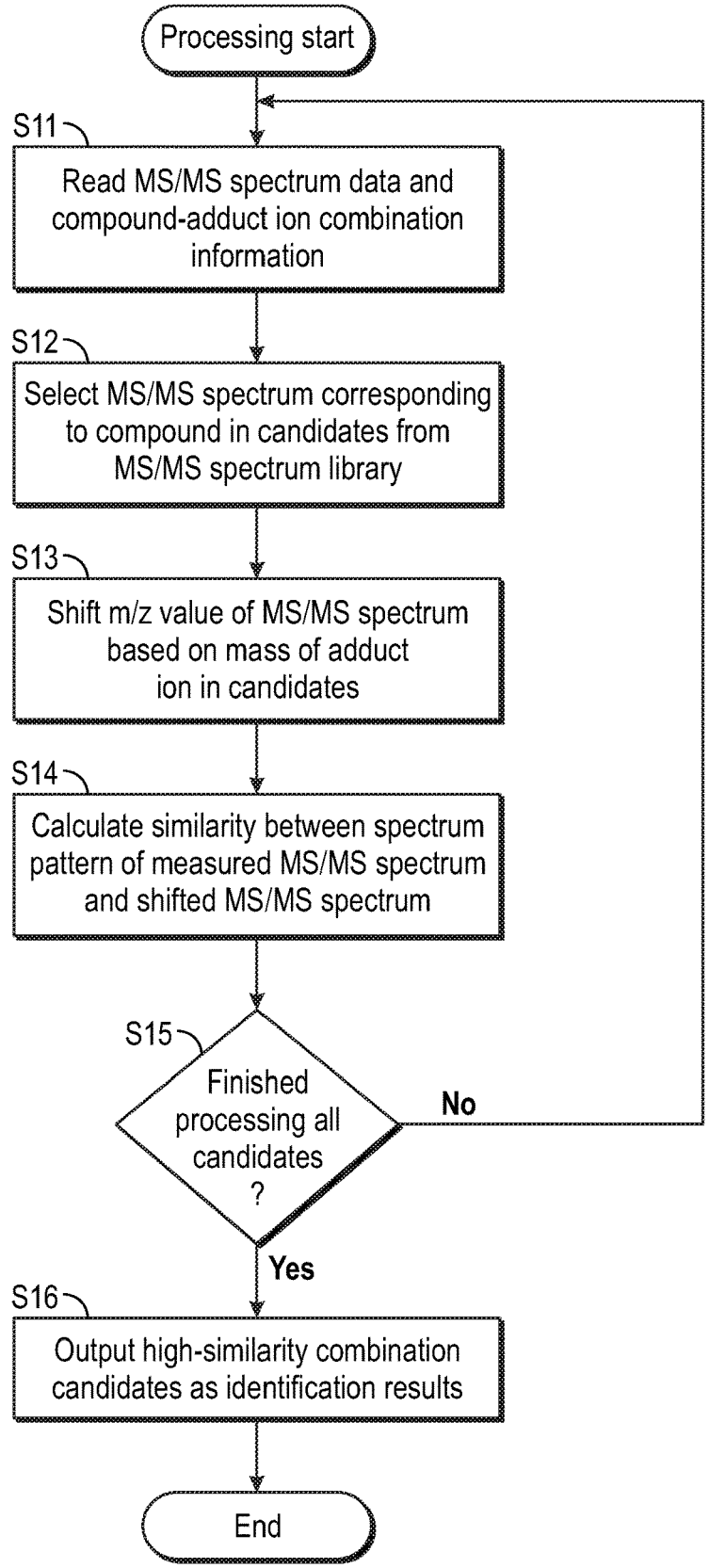
FIG. 9 Flowchart of data processing during an MS/MS spectrum library search in the mass spectroscopy system in this embodiment example.

Next, the characteristic MS/MS library search that is performed by the MS/MS library search portion 24 in the mass spectroscopy system in this embodiment example will be described according to the flowchart shown in FIG. 9.

As described above, a search conducted by compound candidate search portion 23 results in the extraction of candidates for combinations of compounds and adduct ions corresponding to a given peak on a mass spectrum. In contrast, MS/MS spectra contained in an MS/MS spectrum library are typically MS/MS spectra for reference samples of a pure compound on which peaks for proton adduct (or loss) ions of said compound are selected as precursor ions. Accordingly, if the peak specified by the user is not a proton adduct (or loss) ion peak but rather an ion peak for a different ion adduct adducted to the compound, the measured MS/MS spectrum should roughly correspond to the standard MS/MS spectrum stored in the MS/MS spectrum library, but translated along the horizontal axis by a distance corresponding to the difference between the mass of the adduct ion and the proton.

Hence, based on the MS/MS spectrum obtained by performing MS/MS analysis with the mass-to-charge ratio of the specified peak as the precursor ion, MS/MS library search portion 24 identifies the compound by the following procedure.

First, the MS/MS spectrum data subject to processing is read by MS/MS library search portion 24, and information about compound-adduct ion compound candidates associated with the precursor ion are read by the compound search (step S11). Note that information about compound-adduct ion combination candidates can be automatically handed over to MS/MS library search portion 24 from compound candidate search portion 23, or can be input into MS/MS library search portion 24 as per user specification.

MS/MS library search portion 24 selects matching MS/MS spectra of compounds from the MS/MS spectrum library based on the compound-adduct ion combination candidate information (step S12) and then shifts the overall mass-to-charge ratio of the MS/MS spectrum in such a way as to either increase or decrease the mass-to-charge ratio by an amount corresponding to the difference in mass between the adduct ions found with the candidate information and the adduct ions registered in the MS/MS spectrum library. Alternately, in addition to shifting the measured MS/MS spectrum of the adduct ions found with the candidate information, it is also possible to shift the MS/MS spectrum registered in the MS/MS spectrum library by an amount corresponding to the mass of the adduct ions registered in said MS/MS spectrum library (step S13).

Next, the similarity between the spectrum pattern of the shifted MS/MS spectrum and that of the measured MS/MS spectrum (or between the shifted library MS/MS spectrum and the shifted measured MS/MS spectrum) is calculated (step S14). Next, a determination is made as to whether or not a similarity calculation has been performed for all compound-adduct ion combination candidates (step S15), and if some combination candidates remain to be processed, processing returns to step S12. The processing in steps S12~S14 is repeated until the similarity between the measured MS/MS spectrum and the shifted MS/MS spectrum obtained by shifting the standard MS/MS spectrum according to the adduct ion has been calculated for all compound-adduct ion combination candidates.

If step S15 returns a decision of yes, compound-adduct ion combination candidates with the greatest similarity are selected and displayed on the screen of display portion 6 as identification results (step S16). Alternately, a designated number of results can be displayed as a list in descending order of similarity. Thus, even when a compound search is not able to adequately narrow down the compound based on the mass spectrum, the information on compounds and adduct ions obtained from a library search by compound candidate search portion 23 based on the MS/MS spectrum obtained by MS/MS analysis can be used to effectively identify the target compound with a high degree of accuracy.

Note that, when the user selects a peak on the mass spectrum for a compound search or for MS/MS analysis, what appears to be a single peak may in fact represent multiple overlapping peaks of different compounds. Conducting a compound search on such a peak will not be able to adequately narrow down the candidates, while conducting MS/MS analysis of such a peak will result in a complex MS/MS spectrum that is not suited to a library search. Hence, the system in this embodiment example makes it possible for the user to determine whether or not what appears to be a single peak is in fact multiple peaks.

Figure 8:
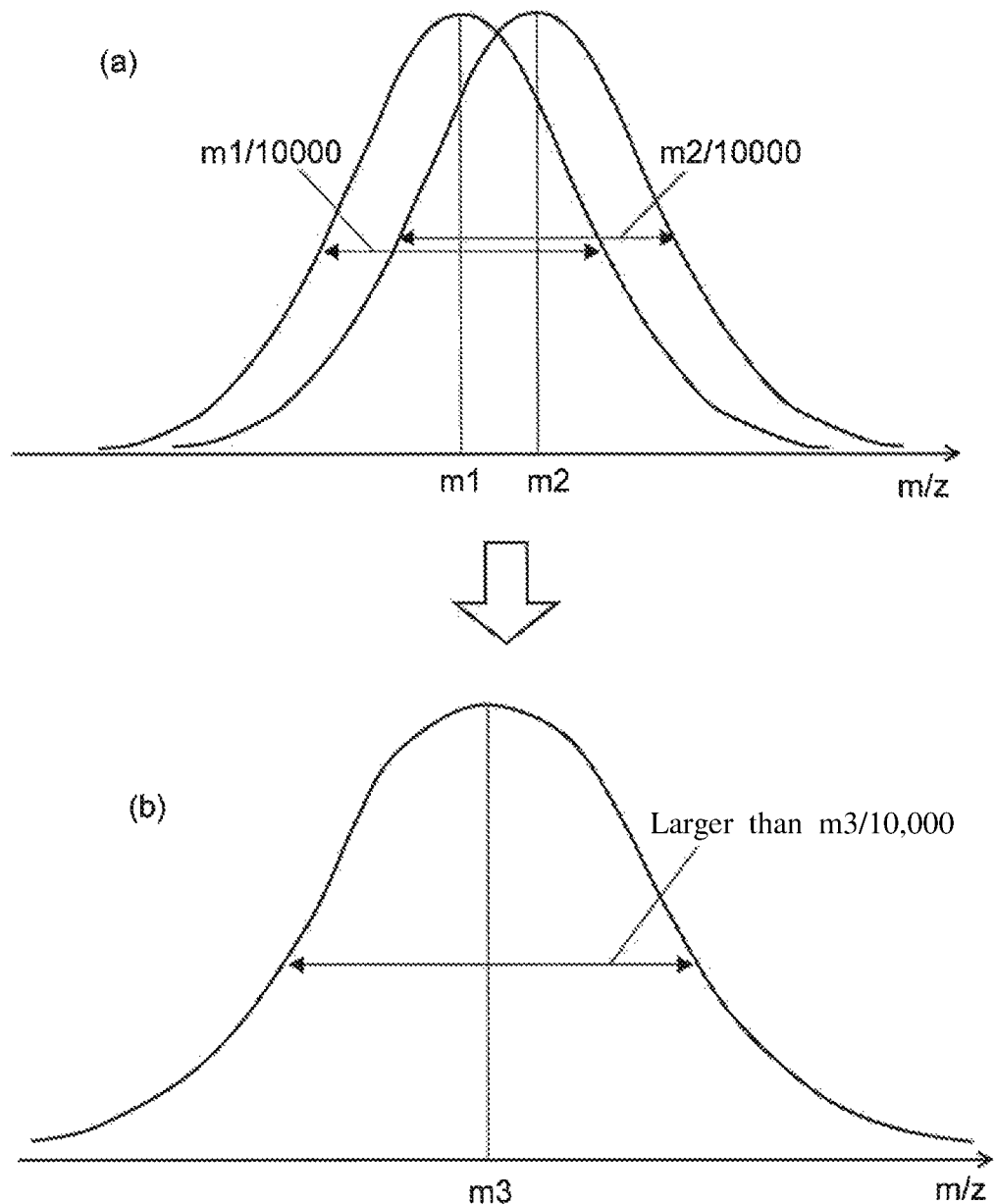
FIG. 8 Diagram illustrating the method used to determine whether or not peaks are overlapping in the mass spectroscopy system in this embodiment example.

In the event that two peaks of compound origin with a slightly different mass-to-charge ratio (m1, m2) are in close proximity, as shown in FIG. 8 at (a), these peaks may in some instances overlap and be observed as a single peak with a mass-to-charge ratio m3 between that of the two peaks (m1<m3<m2), as shown in FIG. 8 at (b). When the mass-to-charge ratio of the center of mass of such overlapping peaks is used in a compound search, there is a chance that the peaks for either compound will not fall within the mass-to-charge ratio margin of error of a typical compound search. In such instances, expanding the mass-to-charge ratio margin of error of the compound search is enough for actual overlapping compound peak information to show up in the search results. In short, as long as it can be determined that several peaks are overlapping, it will at the very least be possible to prevent the actual compounds from being omitted from the search results during a compound search.

Toward this end, when a mass spectrum of the kind shown in FIG. 3 is displayed on the screen of display portion 6 by display processing portion 26, it is displayed superimposed with a zone marking 100 whose peak width is a standard peak width (full width at half maximum) calculated according to the device's mass resolution setting and the mass-to-charge ratio of the location specified by the cursor on the screen. In FIG. 3, this marking 100 is indicated by the shaded portion, but in actual fact can be indicated with any highly visible color.

When the user places the cursor over a given peak, if that peak is an individual peak, the full width at half maximum of that peak should be about the same width as marking 100. However, if the user places the cursor over a peak and said peak is in actuality multiple overlapping peaks, as shown in FIG. 8 at (b), the width of that peak will be considerably wider than the width of marking 100. This allows the user to quickly see that the specified peak may in fact be overlapping peaks for multiple compounds, and hence to take appropriate action when conducting a compound search using that peak, such as using a wider margin of error for the mass-to-charge ratio. This also makes it possible to predict that some candidates arising from multiple compounds may show up in the compound search results.

The mass spectroscopy system in the example embodiment uses MALDI for ionization, which often causes the appearance of peaks of matrix origin on the mass spectrum, or peaks for compound molecules in the sample that have been adducted with matrix molecules. For this reason, compound searches often achieve an adequate level of accuracy by means of algorithms that either include or exclude designated combinations of matrix molecules and adduct ions from the search. Such algorithms can be expanded in the following manner to achieve more general-purpose use or to include or exclude designated combinations of non-matrix compounds and adduct ions.

For example, a field for registering compound names, as well as a field for setting flag information indicating whether or not adduction occurs to that compound, can be added to an adduct ion list of the kind shown in FIG. 6. In short, for each adduct ion, information can be provided indicating a compound name and whether or not adduction occurs to said compound. Rules then need merely be defined, e.g. if the value of this flag is "0," ignore combinations of this adduct ion with compound names in the compound list that match the registered compound name; if the value of this flag is "1," only include combinations with compounds matching the registered compound name; if the value of this flag is "2," only include combinations with compounds that both match the registered compound name and do not have multimers or neutral loss; etc.

Furthermore, during ionization, some compounds ionize as molecular ions without adduct ions. For such compounds, "+" or "−" can be appended to the compositional formula field in the compound list so that, if such a sign is present, combinations thereof with adduct ions in the adduct ion list are to be completely ignored. Alternately, a field can be provided in the compound list to set a flag indicating that ionization occurs in the form of a molecular ion.

In the system in the example embodiment, measurement portion 1 is an imaging mass spectrometer, but it goes without saying that the mass spectroscopy data processing device of the present invention can be applied to any device that processes data obtained from a conventional mass spectrometer. A mass spectrometer capable of MS/MS analysis is of course required to perform an MS/MS library search, but even in this case, a variety of different types of mass spectrometer can be used as the mass spectrometer, including a tandem quadrupole mass spectrometer, Q-TOF mass spectrometer, ion trap mass spectrometer, ion trap-time of flight mass spectrometer, etc.

Furthermore, in the system of the example embodiment, MS/MS library searching was conducted using MS/MS spectra, but it goes without saying that compound identification could equally well be performed by using MSn spectra, where n is 3 or greater, to conduct a library search.

Furthermore, it goes without saying that the above-described embodiment examples and variant examples are only examples of the present invention, and that any appropriate alteration, modification, or supplementation thereto that falls within the scope of the intent of the present invention also falls within the scope of patent claims.

DESCRIPTION OF THE SYMBOLS

1: Measurement portion
10: Ionization chamber
11: Sample stage
12: Sample
13: Laser irradiation portion
14: Vacuum chamber
15: Ion introduction portion
16: Ion guide
17: Ion trap
18: Flight tube
19: Detector
2: Data processing portion
20: Sample information collection portion
21: Spectrum data storage portion
22: Mass spectrum creation portion
23: Compound candidate search portion
24: MS/MS library search portion
25: Library creation/editing portion
26: Display processing portion
27: Identification information memory portion
3: Analysis control portion
4: Primary control portion
5: Input portion
6: Display portion

What is claimed is:

1. A mass spectrometry data processing device that identifies compounds contained in a sample based on mass spectrum data obtained by performing mass spectroscopy of said sample, comprising:
   a) a compound information memory that stores the theoretical mass of a variety of compounds, and, when a compound is ionized under designated ionization conditions, also storing the designated ionization conditions together with a corresponding compound;
   b) an adduct information memory that stores the theoretical mass of adduct ions adducted to a compound during ionization, correlated to the adduct ion, and, when adduction to a compound occurs under designated ionization conditions, also stores the ionization conditions correlated to the adduct ion;
   c) a condition input portion for the user to input ionization conditions during mass spectrometry; and
   d) a compound candidate search portion that finds a measured mass-to-charge ratio of peaks to be identified on a mass spectrum obtained by mass spectrometry and, based on said measured mass-to-charge ratio and the ionization conditions input via the condition input portion, extracts compound and adduct ion combination candidates corresponding to the peaks from among combinations of adduct ions stored in the adduct information memory and compounds stored in the compound information memory.

2. The mass spectrometry data processing device set forth in claim 1, further comprising:
   a display processing portion that displays the compound and adduct ion combination candidates obtained by searching with the compound candidate search portion.

3. The mass spectrometry data processing device set forth in claim 1,
   wherein the device processes data obtained by a mass spectrometer using a MALDI ion source, wherein at least the type of MALDI matrix is included as one of the ionization conditions.

4. The mass spectrometry data processing device set forth in claim 1,
   wherein, in the event that a designated adduct ion is adducted to a compound in a designated type of sample during ionization of said compound, the compound information memory stores the type of the sample associated with the compound, and the adduct information memory stores the type of the sample associated with the adduct ion;

the condition input portion enables input of the type of sample that is subject to mass spectrometry; and the compound candidate search portion can be configured so as to also use information about the type of sample input via the condition input portion to narrow down the results when extracting candidates for combinations of compounds and adduct ions corresponding to the peak.

5. The mass spectrometry data processing device set forth in claim 1, wherein information about neutral loss from a compound when said compound is ionized is also stored associated with that compound in the compound information memory; and the compound candidate search portion is configured so as to use information on neutral loss stored in the compound information memory when extracting candidates for combinations of compounds and adduct ions corresponding to the peak.

6. The mass spectrometry data processing device set forth in claim 1, wherein the compound information memory stores information about the degree of polymerization of a multimer associated with a compound; and the compound candidate search portion is configured so as to use information about multimers stored in the compound information memory when extracting candidates for combinations of compounds and adduct ions corresponding to the peak.

7. The mass spectrometry data processing device set forth in claim 3, wherein the adduct information memory stores identifier information associated with adduct ions indicating whether or not these are adducted to the matrix molecule itself;

the compound information memory stores identifier information associated with the compound indicating whether it is a matrix molecule or multimer thereof; and the compound candidate search portion uses the identifier information stored in the adduct information memory and the compound information memory when extracting candidates for combinations of compounds and ions matching the peak.

8. The mass spectrometry data processing device set forth in claim 2, further comprising a spectrum library for storing MSn spectra associated with compounds;

wherein the compound information memory stores information indicating whether or not MSn spectra are present in the spectrum library, associated with compounds; and the display processing portion is configured so as to display search results in a format that renders it possible to visually determine whether or not an MSn spectrum corresponding to a combination of compound and adduct obtained by searching with the compound candidate search portion is present in the spectrum library.

9. The mass spectrometry data processing device set forth in claim 1, further comprising a spectrum display processing portion that displays the mass spectrum obtained by mass spectrometry on a display screen superimposed with information indicating the standard peak width calculated theoretically based on a pre-set mass resolution and the mass-to-charge ratio of the indicated peak.

* * * * *